United States Patent [19]

Morse et al.

[11] 4,210,178
[45] Jul. 1, 1980

[54] PERPETUAL BY-PASS FLUSHING DEVICE

[76] Inventors: Phillip H. Morse, 310 Ridge St.;
Louis O. Noce, 78 Grant St., both of
Glens Falls, N.Y. 12801; Michael I.
Basta, R.D., Diamond Point, N.Y.
12824

[21] Appl. No.: 823,212

[22] Filed: Aug. 10, 1977

[51] Int. Cl.² .................... F16K 11/07; A61M 5/00
[52] U.S. Cl. .................... 137/625.5; 137/625.42;
128/214 R
[58] Field of Search ........... 137/625.42, 625.5, 625.34,
137/625.37, 605, 625.48; 128/214 R

[56] References Cited

U.S. PATENT DOCUMENTS

| 3,165,120 | 1/1965 | Horowitz | 137/625.37 |
| 3,180,361 | 4/1965 | Worth | 137/625.37 |
| 3,640,277 | 2/1972 | Adelberg | 128/DIG. 12 |
| 3,675,891 | 7/1972 | Reynolds et al. | 128/214 R |

Primary Examiner—Martin P. Schwadron
Assistant Examiner—A. Michael Chambers
Attorney, Agent, or Firm—Kenyon & Kenyon

[57] ABSTRACT

A flushing device for placement in a slow infusion line of liquid to a human or animal body through a catheter, cannula or similar item that provides a flushing or cleaning by-pass route merely by, and only during, finger pressure applied to the flushing actuator.

7 Claims, 7 Drawing Figures

PERPETUAL BY-PASS FLUSHING DEVICE

SUMMARY OF INVENTION

This invention relates to new and useful improvements in a constantly available flushing device to be used in conjunction with slow infusion of liquids into a human or other animal body and more particularly seeks to provide a device having a single channel input and a dual channel output whereby one output is for normal slow infusion flow through the device in its normal state (which is generally under constant known pressure) and the second outflow is for a fast flushing flow which occurs only during the time when simple pressure is applied to an actuator, said actuator being movable, in a direction transverse to the liquid flow direction through the device by the thumb and forefinger of the holding hand, leaving the other hand free for other activity.

PRIOR ART

Catherization laboratories, surgical suites, intensive care units and even normal ward procedures in a hospital constantly call for the infusion of various kinds of liquid from a container into the human body at a controlled and generally fairly slow rate of flow. An attachment may be made to a surface vessel by an I.V. set with a short catheter or cannula or may be made deeper into the body through catheters or other tubular devices. In many cases, between the patient and the liquid source, particularly where there are multi-liquid sources or connections to determine or monitor various blood conditions, such as pressure, heart rate, etc., there may be a manifold or a series of stopcocks in the line. These are provided with valve cores to direct liquid in different directions at various times by an operator turning the valve cores, which is a permanent change until the valve core is changed again. This dictates the need for a manifold or stopcock systems which require careful attention by the operator to flush or clean the systems.

The Reynolds et al. U.S. Pat. No. 3,675,891 provides an in-line flushing device that is applicable to these systems. The Reynolds flushing liquid flow is parallel to the movable axis of the valve, does not stop normal flow during flushing, prevents an elongated obstruction to the flushing flow, and requires two hands of the operator, i.e., one to hold the device and a second to pull the valve stem.

OBJECTS OF THE INVENTION

It is an object of this invention to provide a device that fast flushes only during, and merely by, the application of pressure to a small actuator by one finger of the hand that holds the device in a fixed position.

It is another object of this invention to provide a device that may be used for flushing on momentary notice without use of manifolds, stopcocks or other extraneous equipment.

It is a further object of this invention to provide such a device that is simple enough in construction and economical enough to be used as a one-time, throw-away device if desired.

It is also an object of this invention to provide such a device wherein the actuator moves transversely to the liquid flow and leaves no obstruction in the open side of liquid flow.

From these and other objects, the nature of which will be apparent, the invention will be more fully understood by references to the drawings, the accompanying detailed description and the appended claims.

DESCRIPTION OF THE PREFERRED EMBODIMENT

Figure 1:
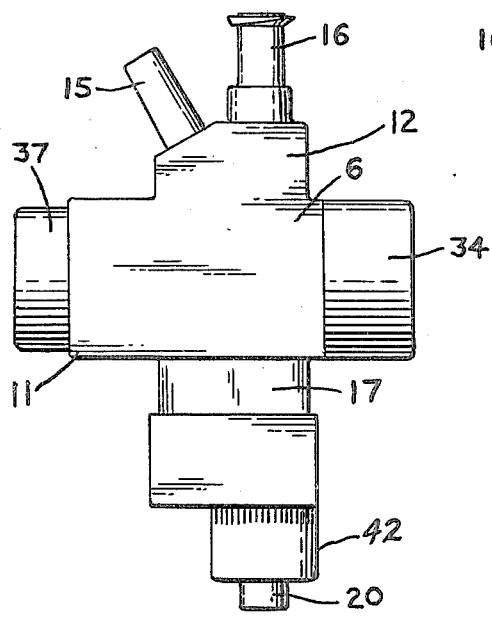
FIG. 1 is a horizontal plan view of a flushing device constructed in accordance with this invention.
Figure 2:
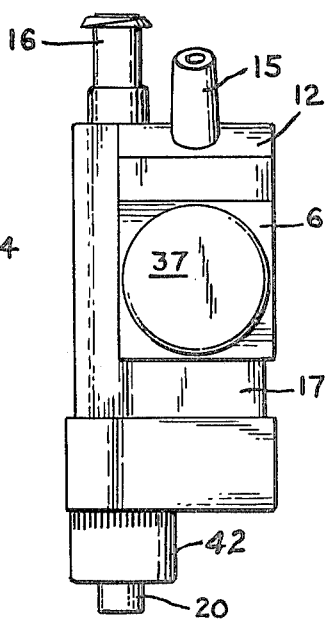
FIG. 2 is a plan view taken from the left of FIG. 1.
Figure 3:
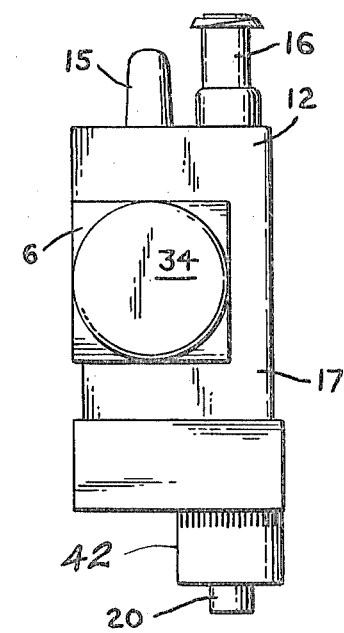
FIG. 3 is a plan view taken from the right of FIG. 1.
Figure 4:
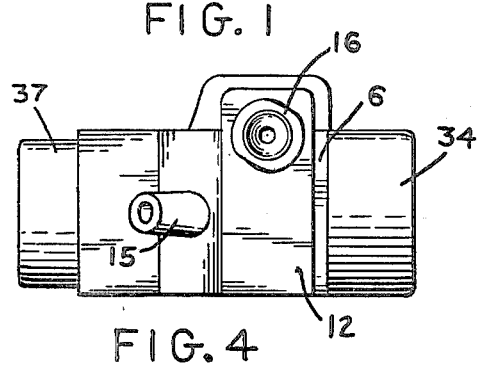
FIG. 4 is a plan view taken from the top of FIG. 1.
Figure 5:
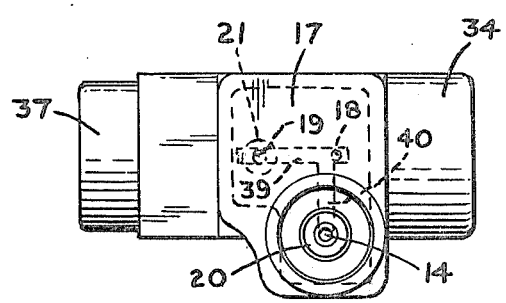
FIG. 5 is a plan view taken from the bottom of FIG. 1.

Referring to the drawings in detail, the invention as illustrated is embodied in a transparent plastic unit designed to be placed in an I.V., arterial or other undwelling line so that fast flushing may be done by merely applying pressure to the actuator by a thumb or finger of the device-holding hand without any further changes being made in the line.

The flushing device includes a transparent housing 6 with a large internal bore 7 extending throughout the width of the housing except for restrictive annular flange 8 which is followed by an even larger bore portion 9 that is defined annularly by end flange 11. An upper dome 12 is provided with an angularly disposed infusion inlet fluid passage 13 and a secondary fluid passage 14 to both of which are attached locking lures 15 and 16, respectively, or other conventional (male or female) means for attaching tubing, needles, or other medical instruments. Secondary fluid passage 14 passes completely through the device to male exit hub 20 which may be any conventional connecting means (male or female). A lower dome 17 is provided with a flushing exit passage 18 and the normal exit passage having a short span 19 with about the same diameter as the flushing passage, and a longer passage 21 immediately below which is much wider than the flushing passage.

Within the internal bore 7 is slidably mounted an elongated cylindrical member 22 that comprises from left to right an activator extension 23, an enlarged annular offset 24, a left O-ring seat 26, an annular fluid passage 27, a right O-ring seat 28, and a spring housing portion 29 which encloses a depressed spring inset 31.

When this is positioned within the bore, left O-ring 32 is mounted in seat 26 and right O-ring 33 is mounted in seat 28, which also serves as bearings and seals when member 22 is moved back and forth within the bore 7. The right end of bore 7 is closed with a cap 34 to enclose spring 36 in the position shown.

The activator extension 23 extends through annular flange 8 into the larger bore portion 9. Adhesively secured to the activator extension is activator button 37 which fits and slides snugly within larger bore portion 9 and extends for approximately a ¼" beyond flange 11 which permits the fingers or other pressure to push the activator button against spring 36 for that distance that the button extends beyond flange 11 in its normal seating capacity when the spring normally forces it to the left.

The lower dome 17 is also enclosed with a cap 38 which provides a channel 39 wherein exit passages 18 and 21 are joined. A second channel 40 is disposed at a right angle to and joins channel 39 with secondary fluid passage 14. Within the larger exit passage 21 is mounted a resistor 41 with a capillary bore 44 as is well known in the art that controls the rate of fluid flow through the exit passage. These capillary bores are commonly sized to control fluid flow at 1, 3, 6, 30, or other cubic centimeters against a 300 mm Hg fluid source pressure. This permits constant flow into, without interference from, the fluid pressure of the patient. The cap is provided with an outlet socket 42 within which is mounted a luer 20 or other similar device for attaching various medical instrumentation.

This device is designed for insertion into an infusion line that is in an artery, vein, heart or other area and will be connected by conventional means and fixtures, such as luers, and the line may contain other conventional equipment, such as filters, I.V. sets, stopcocks, manifolds, catheters, etc. Inlet 16 is particularly adapted for attachment of a transducer but other equipment monitoring and otherwise may be attached at this point or a cap may be placed over this luer if the unobstructed passage is not needed.

Figure 6:
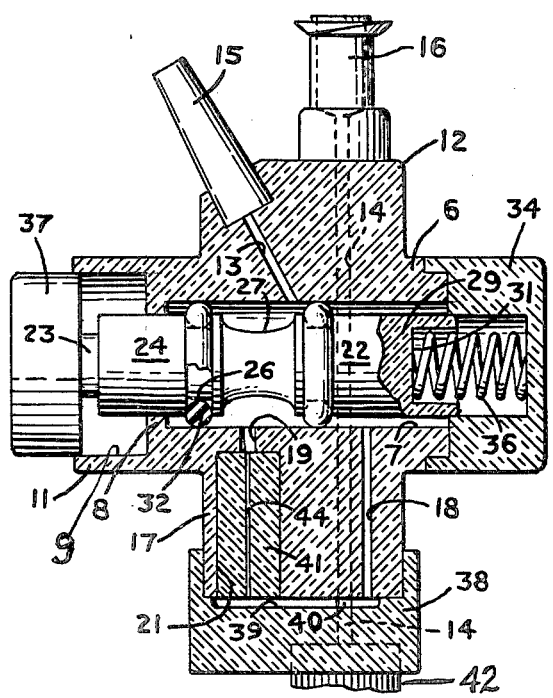
FIG. 6 is a partial section through the large plane of FIG. 1 when the device is in flushing flow position.
Figure 7:
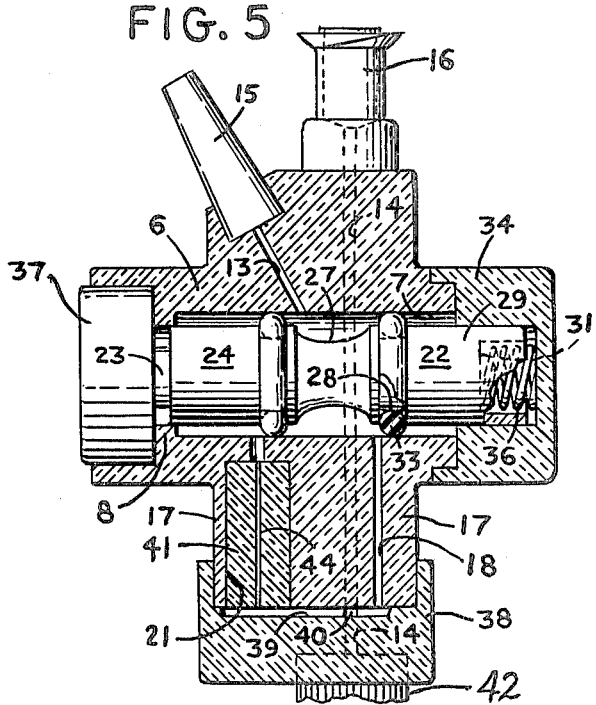
FIG. 7 is a somewhat different partial section when the device is in normal flow position.

The operation of the device is best understood from FIGS. 6 and 7. As shown in FIG. 6, no pressure is being applied to activator button 37 so that spring 36 is forcing cylindrical member 22 to the left. The fluid flow is thus through inlet 13 into the chamber between the two O-rings 32 and 33 and into exit passage 19 through the small bore 44 and resistor 41 which controls the rate of flow, then to exit passage 21 into channel 39, then channel 40 and finally into secondary fluid passage 14 to pass out of the exit hub 20. The by-pass exit passage 18 is blocked by O-ring 33 in FIG. 6 so that the fluid can not pass through that passage.

Then as shown in FIG. 7 the activator button 37 is pushed to the right so that O-ring 32 now blocks exit passage 19 to the restricted bore 44 but has now opened the flushing by-pass exit 18. Thus the fluid flow now from between the O-rings 32 and 33 is through by-pass passage 18 into channel 40 and into the secondary fluid passage 14. The bore 18 being relatively large compared to 44, there is no relative restriction to passage of fluid during the time the device is in the position shown in FIG. 7. The fluid is passed through in relatively high volume for as long as the activator button 37 is pushed to the right and only as long as it is held in that right position. As soon as the activator button is released, the O-rings move to the left and the fluid passage is resumed through the restricted bore 44.

This obviously permits the operator to hold device 6 in one hand and to activate the button 37 with the thumb or one finger without use of the other hand to provide instantaneous, foolproof flushing of the system. Flushing is desired for several purposes, and particularly to prevent clotting at a blood liquid interface which generally is slightly downstream from the tip of the catheter in the vein or artery. If the interface is not maintained at a distance beyond the catheter tip, there is a tendency for clotting to occur at the catheter tip, and since indwelling catheters or cannulae infusions may by for extended periods of time, this risk increases by the amount of time. Therefore, it is helpful to be able to flush the system on a regular basis to overcome any such clotting. Furthermore, there may be other reasons for flushing the system or for adding within the line other materials which it is desired to feed in larger volume rather than the restricted volume required by bore 44.

Various other uses will be apparent to those skilled in the art for the full proof but temporary normal flow by-pass permitted by this device.

We claim:

1. An animal or human infusion flushing device comprising a body having at least a primary passage therethrough, an intermediate portion of said passage being divided into a restricted channel and a flushing channel spaced from each other, liquid directing means comprising valve means movably mounted in said body and movable transversely to said liquid flow through said liquid passage, a pair of sealing means on said valve means defining a space between said sealing means, biasing means for biasing said directing means toward a normal resting position in which said restricted channel is open and said flushing channel is closed, said device being sized to be held in one hand and an extension at one end of said directing means extending outside of said body for exposure to a finger of said holding hand to move said directing means against said biasing means from said resting position to said flushing position in which said flushing channel is open and said restricted channel is closed, said primary liquid passage always communicating with said space, said restricted and flushing channels communicating with said space only when said directing means is in said resting and said flushing position respectively, said body has a secondary liquid passage therethrough generally parallel to said primary passage but independent of said liquid directing means, said secondary passage communicates with said primary passage downstream of said channels.

2. The infusion flushing device of claim 1 wherein said directing means comprises a cylindrical core movable longitudinally within a bore, and said pair of sealing means comprises a pair of spaced O-rings on said core.

3. The infusion flushing device of claim 1 wherein said restricted channel is defined by a marinebase capillary tube.

4. An animal or human infusion flushing device comprising a body having at least a primary passage therethrough, an intermediate portion of said passage being divided into a restricted channel and a flushing channel spaced, from each other, liquid directing means comprising valve means movably mounted in said body and movably transversely to said liquid flow and through said liquid passage, a pair of sealing means on said valve means defining a space between said sealing means, biasing means for biasing said directing means toward a normal resting position in which said restricted channel is open and said flushing channel is closed, said device being sized to be held in one hand and an extension at one end of said directing means extending outside of said body for exposure to a finger of said holding hand to move said directing means aganist said biasing means from said resting position to said flushing position in which said flushing channel is open and said restricted channel is closed, said primary liquid passage always communicating with said space, said restricted and flushing channels communicating with said space only when said directing means is in said resting and said flushing position respectively;

said device including a secondary liquid passage independent of said liquid directing means, said secondary passage communicates with said primary passage downstream of said channels.

5. The infusion flushing device of claim 4 wherein said secondary liquid passage is generally parallel to said primary passage but independent of said liquid directing means.

6. The infusion flushing device of claim 5 wherein said secondary passage communicates with said primary passage downstream of said channels.

7. The infusion flushing device of claim 4 wherein said restricted channel is defined by a marine-bore capillary tube.

* * * * *